(12) United States Patent
Battah

(10) Patent No.: US 10,835,347 B2
(45) Date of Patent: Nov. 17, 2020

(54) TOUCH-FREE MEDICAL INSTRUMENT SANITATION STATION AND METHOD THEREOF

(71) Applicant: Basil Battah, San Antonio, TX (US)

(72) Inventor: Basil Battah, San Antonio, TX (US)

(73) Assignee: SPFM, LP, San Antonio, TX (US)

( * ) Notice: Subject to any disclaimer, the term of this patent is extended or adjusted under 35 U.S.C. 154(b) by 895 days.

(21) Appl. No.: 13/897,072

(22) Filed: May 17, 2013

(65) Prior Publication Data

US 2013/0306105 A1 Nov. 21, 2013

Related U.S. Application Data

(60) Provisional application No. 61/648,177, filed on May 17, 2012.

(51) Int. Cl.
*A61B 90/70* (2016.01)
*A61B 7/02* (2006.01)

(52) U.S. Cl.
CPC ........... *A61B 90/70* (2016.02); *A61B 7/02* (2013.01); *A61B 2090/701* (2016.02)

(58) Field of Classification Search
CPC .................................. A61B 19/34; A61B 7/02
USPC ....................................................... 422/290
See application file for complete search history.

(56) References Cited

U.S. PATENT DOCUMENTS

| 2003/0052136 | A1* | 3/2003 | Weng ..................... | A47K 10/32 |
| | | | | 222/192 |
| 2009/0238738 | A1* | 9/2009 | Hurwitz .................. | A61L 2/18 |
| | | | | 422/292 |
| 2010/0116841 | A1* | 5/2010 | Perlman ................. | A61B 90/70 |
| | | | | 221/222 |
| 2010/0117836 | A1* | 5/2010 | Seyed Momen ......... | G01S 1/70 |
| | | | | 340/573.1 |
| 2013/0337243 | A1* | 12/2013 | Ishikawa ................ | A47K 10/16 |
| | | | | 428/211.1 |
| 2015/0047645 | A1* | 2/2015 | Jumisco .................. | A61F 6/04 |
| | | | | 128/844 |

FOREIGN PATENT DOCUMENTS

JP 2004065269 A * 3/2004

OTHER PUBLICATIONS

English Translation of Japanese Document No. JP 2004-065269 A provided by the Japan Platform for Patent Information: Mogami Shotaro; Sanitary Tissue; Apr. 3, 2004.*

* cited by examiner

*Primary Examiner* — Kevin Joyner
(74) *Attorney, Agent, or Firm* — David G. Henry, Sr.

(57) ABSTRACT

A cleansing unit for enhanced sanitation compliance and for eradicating a healthcare facility-hosted opportunistic infections, the unit comprising: a hands-free automatic dispenser of disinfectant agent that dispenses such agent either directly on at least one agitation membrane support post having a condom-like mounted textured sheath or directly on the auscultation portion of the stethoscope, said textured sheath designed to provide a frictional agitation of an auscultation portion of a stethoscope to effectively clean and sanitize the stethoscope, and method thereof.

6 Claims, 5 Drawing Sheets

TOUCH-FREE MEDICAL INSTRUMENT SANITATION STATION AND METHOD THEREOF

CROSS-REFERENCE TO RELATED APPLICATIONS

This U.S. Utility Application claims priority pursuant to 35 U.S.C. § 119(e) to the following U.S. Provisional Patent Application, the specification of which is incorporated herein by reference for all purposes: U.S. Provisional Application Ser. No. 61/648,177, titled "TOUCH-FREE MEDICAL INSTRUMENT SANITATION STATION," filed May 17, 2012.

FIELD OF THE INVENTION

The present invention relates to medical instrument care and sterilization systems and methods.

BACKGROUND OF THE INVENTION

There exists today, as never before, a near epidemic of healthcare facility-hosted opportunistic infections that are transmitted primarily to the very young, the very old, and the immuno-suppressed. These three populations are in the majority in every hospital population around the country. The incredible rise of one of the deadliest germs is Methicillin-Resistant *Staphylococcus aureus* (MRSA) infections in healthcare facilities, as well as other infections involving antibiotic-resistant strains renders the present situation a national healthcare emergency.

Proper aseptic technique is essential in minimizing such infections. Simple procedures such as frequent hand-washing and proper cleansing of medical equipment can all be used to help prevent the spread of infections. Such drastic measures as "single use medical devices" have been proposed to help solve this problem, but cost implications render this approach impracticable, particularly in the current climate of budget constraints and pressure to arrest, if not reverse, the growth of healthcare spending.

One source of potential infection for patients is the common stethoscope. Virtually every physician or other healthcare provider with direct patient access has this instrument, and contacts patients with it dozens of times each working day. It is reported that, of the estimated 30 million stethoscopes in use today, less than 2% are cleaned between patient assessments.

A traditional stethoscope consists of a head portion for collecting sounds (an auscultation portion), one or two sound tubes that transport the sounds, and two ear-pieces that fit inside the ears of the user. The head portion includes a large diaphragm opposed to a smaller bell. The diaphragm or the bell is pressed against the skin of a patient to collect high or low frequency sounds. The auscultation portion of the stethoscope (whether the diaphragm or the bell) harbors untold numbers of germs. If doctors and nurses were given a simple, quick, convenient way to sterilize their stethoscope diaphragms they would be much more likely to perform this simple, yet crucial task.

As with any prophylactic approach to health or safety, ease and convenience of use is paramount in achieving high compliance levels. Having to seek out a disinfectant (alcohol, for example) and apply it with a separate applicator (a cotton swab or patch, for example) is, in reality, a high barrier to consistent stethoscope sterilization.

Despite plentiful art, there exists, therefore, a dire need for providing, not just effective means for cleaning stethoscopes between each use, but that such means are both cost-effective and extremely convenient for use by practitioners. Further still, such means should, in an ideal case, be such that their use may not easily be forgotten or overlooked.

Accordingly, an improved system and method to encourage increased stethoscope's cleansing compliance in environments where the transfer of pathogens can be dangerous remains highly desirable.

SUMMARY OF THE INVENTION

In view of the foregoing, it is an object of the present invention to provide a useful apparatus for preventing the spread of opportunistic infections in a medical setting.

It is also an object of the present invention to provide an improved system and method to encourage increased stethoscope cleansing compliance by increased convenience and simplicity of the apparatus to use.

It is another object of the present invention to benefit medical personnel and patients by giving the medical personnel an easy, fast, convenient way to sterilize stethoscope diaphragms between patient assessments.

It is a further object of the present invention to have a stethoscope cleansing unit available in each examining room with the medical personnel and patient so that medical personnel will be reminded and motivated to cleanse their stethoscopes between patient assessments.

In satisfaction of these and other related objectives, Applicant's present invention provides a "hands-free" dispenser of disinfectant agent that dispenses such agent on an agitation member (or directly on the diaphragm or the bell of the stethoscope) for "scrubbing" the diaphragm to effectively clean and sanitize it. The preferred embodiment of the invention is one that is readily recognized in any examination context and, therefore, not easily overlooked.

The preferred embodiment includes at least one post or similar member for supporting a replaceable, textured sheath that provides the desired frictional agitation of a diaphragm surface for optimal efficacy in sanitizing the device.

It is yet another object of the present invention to provide a stethoscope sanitizing device that can be used with stethoscopes of varying sizes including adult and pediatric stethoscopes.

According to one embodiment of the present invention, the diaphragm or the bell of the stethoscope could be mechanically scrubbed over the textured sheath of at least one agitation post by physically moving an auscultation portion of the stethoscope over the textured sheath after the disinfectant is evenly spread over the auscultation portion of the stethoscope. Another method of mechanically cleansing (scrubbing) a diaphragm could be invoked by the rotational movement of the post powered by a small motor. In one embodiment of the present invention, the motor powers a plurality of agitation posts positioned in relation to each other in close (parallel) proximity so as to augment the overall surface available for the scrubbing.

Applicant's approach to the problem described above is certainly simple, but it is equally unobvious. Applicant's apparatus and novel method facilitate for the first time a solution to the problem of how to quickly and easily sterilize a stethoscope diaphragm.

DETAILED DESCRIPTION OF THE PREFERRED EMBODIMENT

With reference to FIGS. 1-5, the stethoscope sanitation unit of the present invention is identified generally by the reference number 10.

Figure 1:
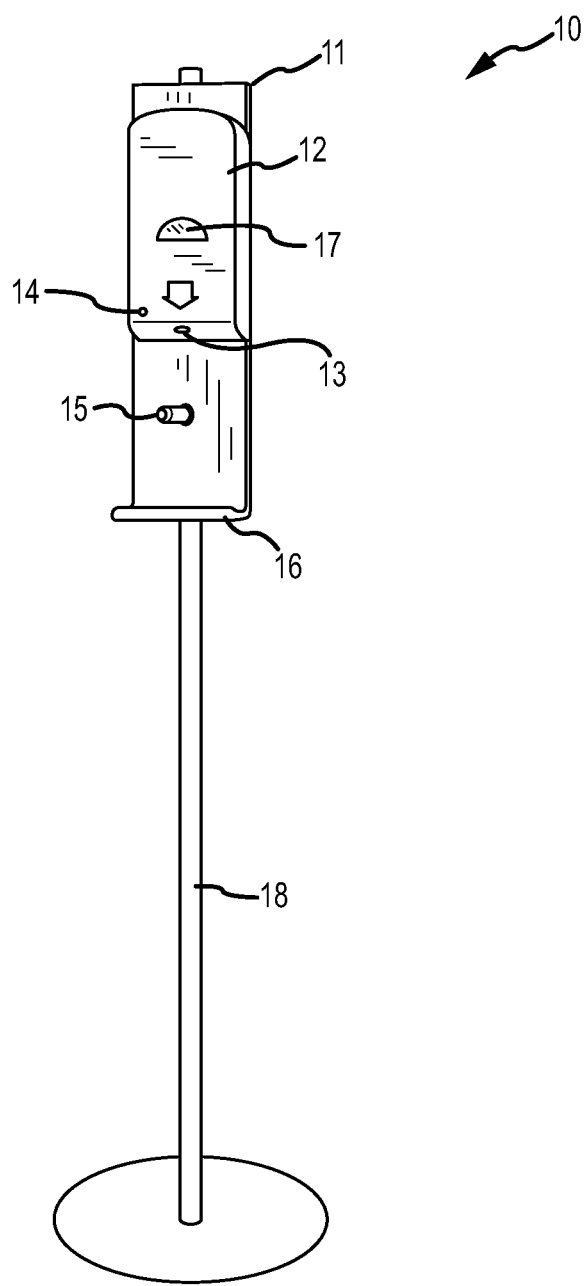
FIG. 1 is a perspective view of the stethoscope cleansing unit of the present invention depicted in a floor stand installation.

In FIG. 1, a cleansing unit 10 includes an overall housing 11 that supports a disinfectant holding chamber 12 having a bottom dispensing nozzle 13 and a sensor 14, an agitation membrane support post 15, and a lower, catch tray 16 located below the dispensing nozzle 13 of the dispensing chamber 12 by which drippings and excess dispensed amounts are caught by the tray 16 and do not fall upon the floor therebelow. In the preferred embodiment, the disinfectant holding chamber 12 would host a measure of disinfecting liquid (isopropyl alcohol, for example). However, part of front covering of the overall housing has a clear opening 17 (also shown in FIG. 3 (32)) allowing constant monitoring of the level of disinfectant available for future users, including pre-measured "critical" line showing that the depletion in the disinfectant requires immediate attention of the supply personnel to refill the disinfectant. The disinfectant holding chamber 12 itself might serve as the actual light-tight vessel in which sanitizing agent is poured, but more likely bladders or other replacement cartridges (not shown) and the like will be placed within the disinfectant holding chamber 12. The housing 11 of unit 10 is coupled with the pole stand 18 supporting housing 11.

Consistent with existing technologies for hands-free dispensers, dispensing of a spray of disinfectant liquid toward post 15 will occur whenever something comes between the disinfectant holding chamber 12 and post 15. According to one embodiment of the present invention, when a healthcare provider extends the auscultation portion of the stethoscope (a diaphragm or a bell) towards a disinfectant holding chamber 12 and positions the stethoscope's auscultation portion underneath the chamber 12, the chamber 12 automatically dispenses a portion of sanitizing gel or foam (or any other type of sanitizing product) onto the diaphragm (e.g., via infrared sensor, motion sensor, capacitive flux sensor, etc such as one shown in FIG. 1 (14)). Such a touch free sanitizer 12 maybe powered by batteries or otherwise coupled to pump dispenser for a power source. Touchless automatic dispensers (of disinfectant liquids or towels) introduced in recent years provide better hygiene and superior dispensing control. Such dispensers are seen in following patents: Dispenser, Sensor, method and System with Proximity Sensor, U.S. Pat. No. 6,592,067 to Denen et al., which discloses and claims an apparatus dispensing paper upon detection of a hand next to it, and which has a movement sensor containing an electrical circuit measuring change of capacitance as a result of proximity of a hand; see also Proximity Detection Circuit and Method of Detecting Small Capacitance Changes, U.S. Pat. No. 6,838,887 where there is described a second miniaturized circuit that is added for detecting proximity of a hand (a proximity sensor embodiment comprises a circuit according to a balanced bridge principle where detection is based on detecting a phase difference, which depends upon the amount of detected capacitance difference or change of capacitance in a region of detection); as well as Static Build Up Electronic Dispensing System, U.S. Pat. No. 6,871,815 to Moody et al., which provides for a system for dissipating static electrical build up to local ground via a metal contact between the high conductivity pathway and, for example, the wall against which the dispenser is mounted. Other examples of touchless dispenser assembly known to one skilled in the art could be used such as the dispenser assembly for dispensing disinfectant fluid as described in U.S. Application Publication No. 2012/0218106 and incorporated herein for all purposes. In essence, the system and method includes detecting a user. An electronic unit is coupled to the main housing. The electronics unit includes a controller and sensor for detecting the activation signal. The electronic transmitter is activated to generate the activation signal in response to detecting the user. Another example of the automatic dispensers suitable in the present invention are described in U.S. Pat. Nos. 6,209,752 and 8,353,427, which references are incorporated by reference herein in their entirety. In there, the automatic dispensing apparatus that is powered using rechargeable battery pack rechargeable via solar cells is disclosed.

Figure 4:
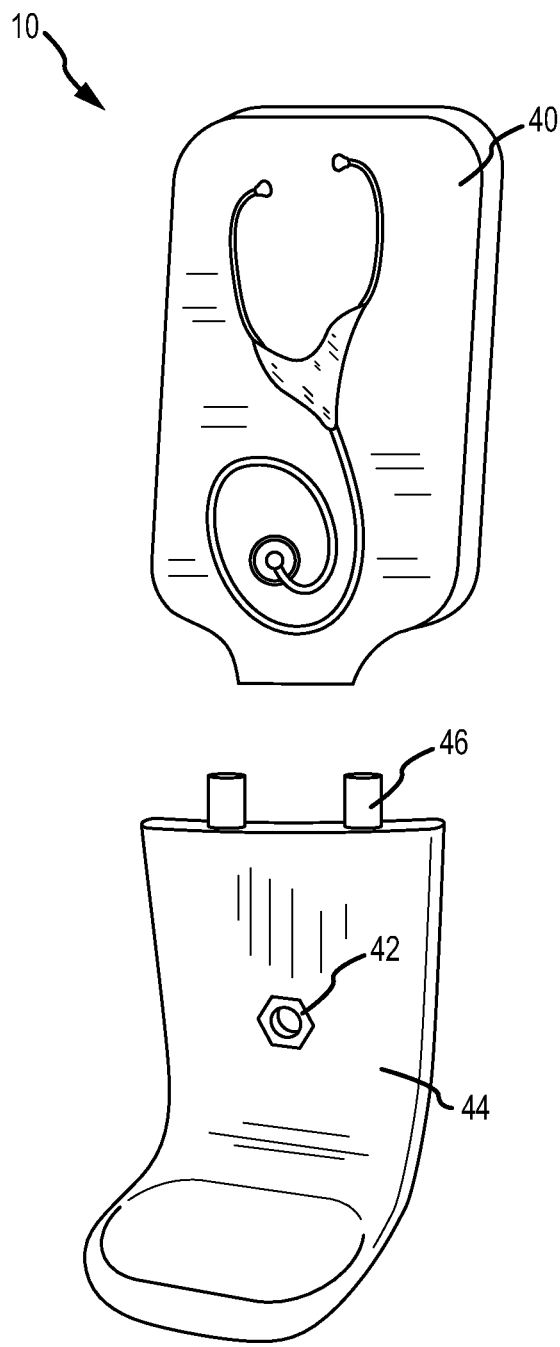
FIG. 4 is a perspective view of the stethoscope cleansing unit that could be mounted on the wall showing means for attaching the agitation member (post) for scrubbing the auscultation portion of the stethoscope.
Figure 5:
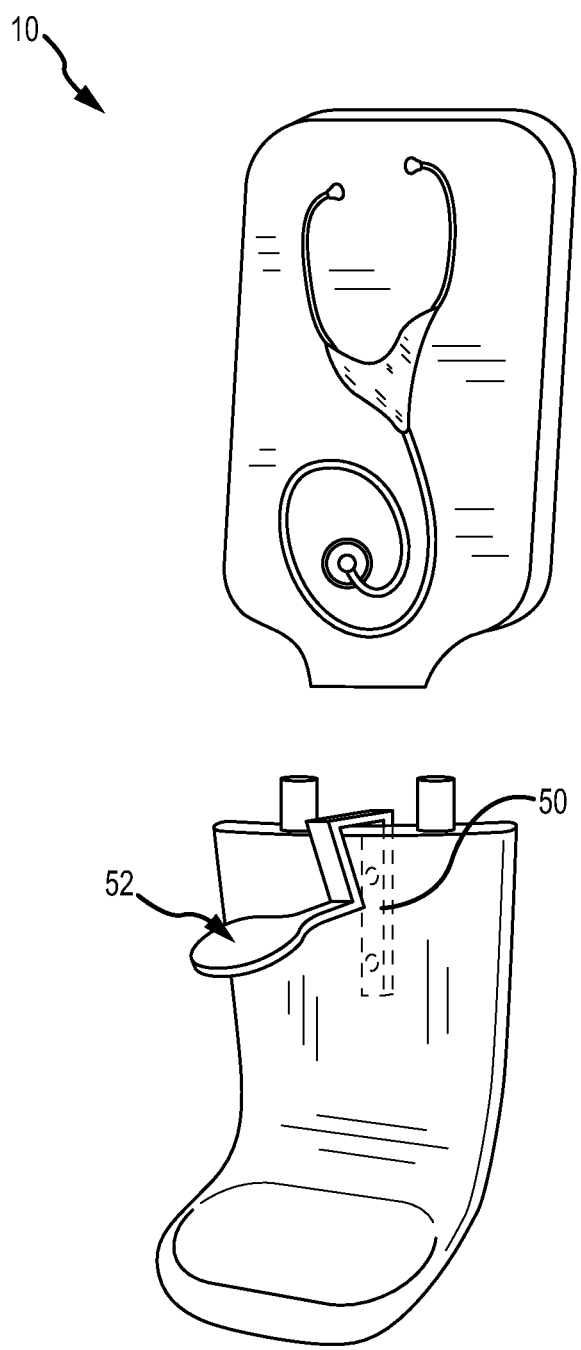
FIG. 5 is another perspective view of the stethoscope showing "spatula-like" agitation post with an L-shaped attachment mounted to the back side of the catch tray portion of the cleansing unit according to one embodiment of the present invention.

The preferred embodiment of the present invention contemplates a pole stand 18 coupled with the overall housing 11 of the cleansing unit 10 (FIG. 1). In another embodiment, the cleansing unit 10 (without the pole) is configured for mounting on a wall for use in a public area (FIGS. 3-5).

Figure 2:
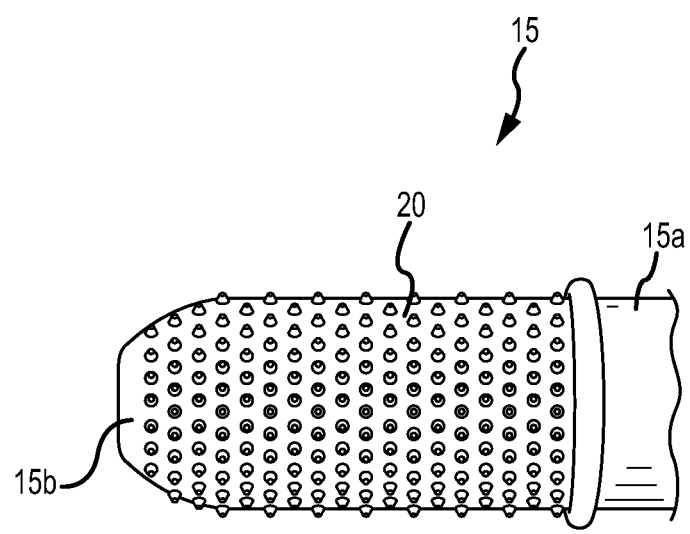
FIG. 2 is an elevational view of one embodiment of a textured sheath used as an agitation member in preferred embodiments of the present invention.

Referring particularly to FIG. 2, the preferred embodiment of the present invention includes a replaceable, textured, condom-like agitation membrane 20 that is mounted on the outwardly projecting post 15 (FIGS. 1 and 2). In one embodiment of the present invention, post 15 is a projecting or a protruding knob or protuberance, having an attachment end 15a attached to the housing 11 of the cleansing unit 10 by conventional means such as pivots, posts, or could be screwed in, and a free end 15b configured to receive a replaceable agitation membrane 20. Alternatives structures for this agitation membrane 20 may include fabric or nonwoven material sheaths or tubes. The primary objective for agitation membrane 20 is to provide a textured ("rough") surface that, when a disinfectant agent is applied to it, serves to "scrub" the stethoscope diaphragm to achieve optimal, realistic levels of sterilization.

Figure 3:
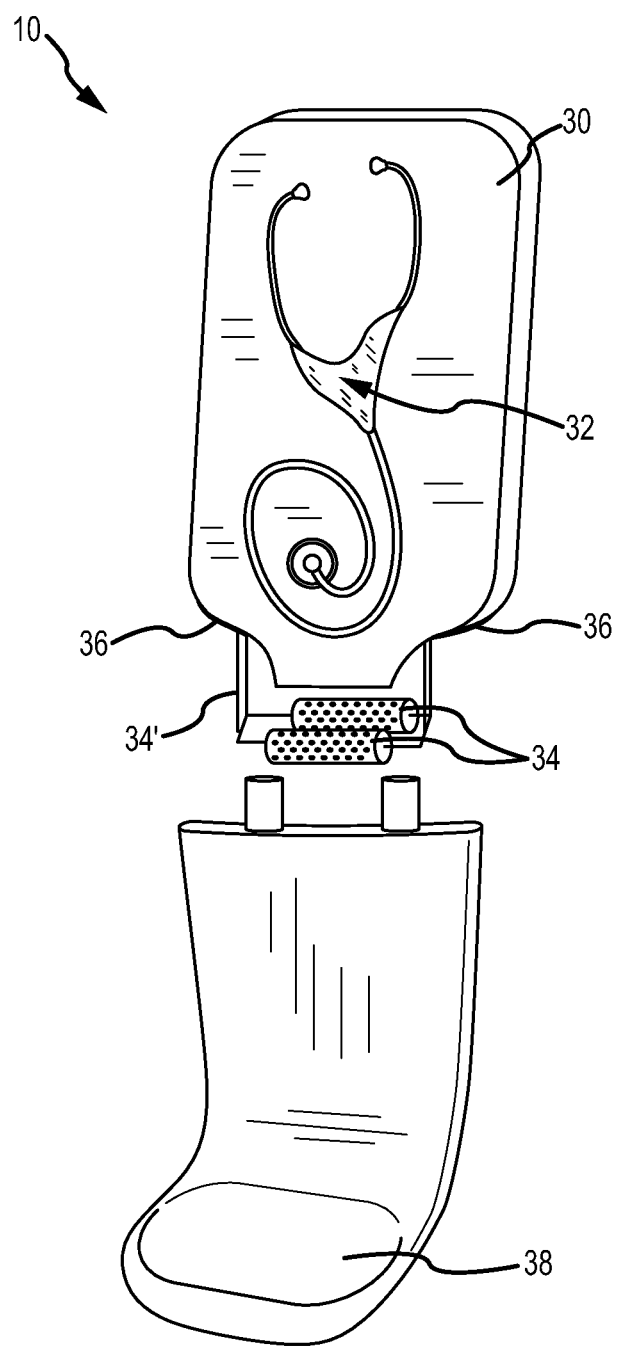
FIG. 3 is a perspective view of a stethoscope cleansing unit that could be mounted on the wall showing a plurality of agitation members for scrubbing the auscultation end of the stethoscope.

In FIG. 3, according to a second embodiment thereof, there are plurality of spaced apart agitation membrane support posts 34 that are positioned parallel with respect to one another and substantially parallel to the catch tray 38. According to one embodiment of the present invention, the posts 34 could be mounted inside the housing of the disinfectant holding chamber 30 but below the disinfectant holding chamber's spray nozzle (not shown). Yet according to another embodiment of the present invention, the post 34 may be mounted outside the housing of the disinfectant holding chamber 30 and below the disinfectant holding chamber's spray nozzle (as shown in FIG. 3). The chamber 30 has movement sensors 36, said sensors are being activated whenever the diaphragm of the stethoscope comes close to either of the sides of chamber 30. A pre-determined amount of disinfectant is dispensed on the plurality of posts 34 to allow scrubbing of the diaphragm over the textured agitation membrane mounted on the posts 34.

According to one embodiment of the present invention, the posts 34 are powered by motor housed inside the disinfectant holding chamber 30. Yet, according to another embodiment of the present invention, the posts 34 are installed on the rolling member 34' and coupled together to allow free rolling (without the involvement of the motor) of both posts whenever the diaphragm comes in contact with said posts and is physically moved (scrubbed) over the surface of the posts 34.

According to one embodiment of the present invention, the spacing between the posts 34 is up to approximately 1 mm wide to allow for an enhancement of the overall surface available for the diaphragm of the stethoscope to be effectively scrubbed over the agitation membrane during the cleansing process.

According to one embodiment of the present invention, the posts 34 are moved by a conventional motor housed inside the chamber 30 (not shown) and powered by rechargeable batteries. The movement exerted on the posts by the motor might be of rotational type or, simply an oscillation type to agitate the sheath disposed over the posts. The start of the motor allowing agitation of the post is synchronized with the dispensing of the disinfectant through the sensors 36 being activated by the movement of the diaphragm of the stethoscope into the proximity of the sensors on either side of the chamber 30.

Turning to FIG. 4, there is an imbedded hex nut 42 shown as an example of the attachment means to which post 15 (FIG. 1) is attached in a wall mounting disinfectant unit 10. In a wall mounting unit, the disinfectant holding chamber 40 may be attached to the catch tray portion 44 of the cleansing unit 10 by the mounting posts 46.

In FIG. 5, according to yet another embodiment of the present invention, the agitation membrane support post 52 takes the shape of a "spatula like" post and is attached through a conventional attachment means (through the L-shaped attachment) to a back side of a catch tray portion 50 of the cleansing unit 10. The spatula like attachment 52 is configured to receive a textured agitation membrane to allow mechanical scrubbing of the diaphragm.

Though not shown in the drawings, dispensers of agitation membranes may be attached to, or somehow provided adjacent to units 10 (again, for providing optimal convenience, and with it, the highest possible compliance in use).

While there are other stethoscope cleaning systems available (see, for example, U.S. Pat. No. 7,282,177 issued in Castaneda, and the relevant art cited herein), none provide the ease of use, noticeable presence in a healthcare context, nor cost effectiveness that will lead to high adoption and compliance rates.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

What is claimed is:

1. An apparatus for eradicating a healthcare facility-hosted opportunistic infections, the apparatus comprising:
   at least one textured membrane replaceably attached to an agitation membrane support structure, wherein said at least one textured membrane is designed to provide a frictional agitation of an auscultation portion of a stethoscope, wherein said at least one textured membrane has at least one raised agitation surface wherein said agitation membrane support structure positioned remote from said housing; and
   a hands-free automatic disinfectant holding chamber of a disinfectant agent, said chamber being contained in a housing and configured to directly dispense said disinfectant agent on said auscultation portion of a stethoscope when disposed beneath said housing.

2. The apparatus of claim 1, further comprising a plurality of agitation membrane support structures wherein each agitation membrane support structure of said plurality of agitation membrane support structures is spaced within approximately up to 1 mm of each other, and wherein said plurality of agitation membrane support structures includes said agitation membrane support structure.

3. The apparatus of claim 2, wherein said each agitation membrane support structure of said plurality of agitation membrane support structures is substantially parallel to each other.

4. The unit of claim 1, further comprising a catch tray.

5. The unit of claim 1, wherein said at least one textured membrane is disposable.

6. The apparatus of claim 1 wherein said at least one textured membrane is substantially cylindrical.

* * * * *